(12) United States Patent
Holmes et al.

(10) Patent No.: US 9,992,818 B2
(45) Date of Patent: Jun. 5, 2018

(54) PROTOCOL TRANSLATION DEVICE

(71) Applicant: MEDTRONIC MINIMED, INC., Northridge, CA (US)

(72) Inventors: Alexander E. Holmes, La Canada, CA (US); Darren Y. K. Yap, Valencia, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days. days.

(21) Appl. No.: 14/876,477

(22) Filed: Oct. 6, 2015

(65) Prior Publication Data

US 2017/0099698 A1   Apr. 6, 2017

(51) Int. Cl.
| | |
|---|---|
| H04W 80/06 | (2009.01) |
| H04B 1/40 | (2015.01) |
| H04B 1/3883 | (2015.01) |
| A61B 5/00 | (2006.01) |
| H04W 88/06 | (2009.01) |
| H04L 29/06 | (2006.01) |

(52) U.S. Cl.
CPC ........... *H04W 80/06* (2013.01); *A61B 5/0015* (2013.01); *H04B 1/3883* (2013.01); *H04B 1/40* (2013.01); *H04L 69/08* (2013.01); *H04W 88/06* (2013.01)

(58) Field of Classification Search
USPC .......................................................... 455/74
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |

(Continued)

FOREIGN PATENT DOCUMENTS

| | | |
|---|---|---|
| EP | 1611838 A1 | 1/2006 |
| WO | 2004032994 A2 | 4/2004 |
| WO | 2004032994 A3 | 4/2004 |

OTHER PUBLICATIONS

PCT International Search Report for Application No. PCT/US2016/053767 dated Dec. 13, 2016.

*Primary Examiner* — Edward Urban
*Assistant Examiner* — Ralph H Justus
(74) *Attorney, Agent, or Firm* — Medtronic Minimed, Inc.

(57) ABSTRACT

A protocol translation device for use with a first apparatus having a battery compartment and communicating over a first wireless protocol, and for use with a second apparatus communicating over a second wireless protocol. The protocol translation device can include a battery casing sized to fit within the battery compartment, the battery casing defining an interior volume; a translator having a first antenna operable to communicate with the first apparatus, a second antenna operable to communicate with the second apparatus, and a translator circuit operably connected between the first antenna and the second antenna; and a battery operably connected to power the translator. The translator circuit is operable to translate between the first wireless protocol and the second wireless protocol. The translator and the battery are disposed within the interior volume.

16 Claims, 5 Drawing Sheets

(56) References Cited

U.S. PATENT DOCUMENTS

| | | |
|---|---|---|
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2004/0071123 A1 | 4/2004 | Shin |
| 2005/0113054 A1* | 5/2005 | Lee ............ H04B 1/3883 455/270 |
| 2007/0123819 A1 | 5/2007 | Mernoe et al. |
| 2007/0188343 A1* | 8/2007 | Sulc ............ H04B 1/0067 340/13.25 |
| 2007/0222681 A1 | 9/2007 | Greene et al. |
| 2010/0113111 A1* | 5/2010 | Wong ............ H01Q 1/243 455/575.5 |
| 2010/0160861 A1 | 6/2010 | Causey, III et al. |
| 2011/0050164 A1* | 3/2011 | Partovi ............ H01F 5/003 320/108 |
| 2011/0163880 A1 | 7/2011 | Halff et al. |
| 2012/0244805 A1* | 9/2012 | Haikonen ......... H04W 52/0274 455/41.2 |
| 2015/0173674 A1* | 6/2015 | Hayes ............ A61B 5/681 600/301 |
| 2015/0312380 A1* | 10/2015 | Sauerbrey ............ H04L 69/08 455/426.1 |
| 2015/0324918 A1* | 11/2015 | Ward ............ G06Q 40/06 705/36 R |
| 2015/0325918 A1* | 11/2015 | Ito ............ H01Q 1/243 343/702 |

* cited by examiner

PROTOCOL TRANSLATION DEVICE

TECHNICAL FIELD

The technical field of this disclosure is wireless communication devices, particularly, protocol translation devices.

BACKGROUND OF THE INVENTION

Advances in electronics and telemetry have resulted in the miniaturization of personal electronic devices such that electronic devices which previously required large stationary equipment can now be worn about the person. Such electronic devices are often powered by batteries stored in a battery compartment and are able to communicate with other electronic devices in their vicinity.

Communication protocols for communication between electronic devices evolve over time with hardware and software improvements to provide faster, more reliable communication. Unfortunately, existing electronic devices are stuck with the communication protocol with which they were built. Newer communication protocols required to interact with newer external devices are often different than the original communication protocol available in an older, as-built electronic device. Although the older electronic device remains capable of performing its original function, it is unable to interact with the newer devices and to take advantage of their improvements and additional features.

It would be desirable to have a protocol translation device that would overcome the above disadvantages.

SUMMARY OF THE INVENTION

One aspect of the invention provides a protocol translation device for use with a first apparatus having a battery compartment and communicating over a first wireless protocol, and for use with a second apparatus communicating over a second wireless protocol, the protocol translation device including: a battery casing sized to fit within the battery compartment, the battery casing defining an interior volume; a translator including a first antenna operable to communicate with the first apparatus, a second antenna operable to communicate with the second apparatus, and a translator circuit operably connected between the first antenna and the second antenna, the translator circuit being operable to translate between the first wireless protocol and the second wireless protocol, being operable to communicate with the first antenna on the first wireless protocol, and being operable to communicate with the second antenna on the second wireless protocol; and a battery operably connected to power the translator; wherein the translator and the battery are disposed within the interior volume.

Another aspect of the invention provides a protocol translation device for use with a first apparatus having a battery compartment and communicating over a first wireless protocol, and for use with a second apparatus communicating over a second wireless protocol, the protocol translation device including: a battery casing sized to fit within the battery compartment, the battery casing defining an interior volume; a translator including a first antenna operable to receive a first-in signal from the first apparatus, the first-in signal conforming to the first wireless protocol, a translator circuit operable to receive the first-in signal from the first antenna and operable to translate the first-in signal to a second-out signal conforming to the second wireless protocol, and a second antenna operable to receive the second-out signal from the translator circuit and operable to transmit the second-out signal to the second apparatus; and a battery operably connected to power the translator; wherein the translator and the battery are disposed within the interior volume.

Another aspect of the invention provides a protocol translation device for use with an insulin pump having a battery compartment sized to fit a AAA battery and communicating over a 916.5 MHz OOK protocol, and for use with a smart phone communicating over a Bluetooth protocol, the protocol translation device including: a battery casing sized to a AAA battery form factor, the battery casing defining an interior volume; a translator including a first antenna operable to communicate with the insulin pump, a second antenna operable to communicate with the smart phone, and a translator circuit operably connected between the first antenna and the second antenna, the translator circuit being operable to translate between the 916.5 MHz OOK protocol and the Bluetooth protocol, being operable to communicate with the first antenna on the 916.5 MHz OOK protocol, and being operable to communicate with the second antenna on the Bluetooth protocol; and a rechargeable battery operably connected to power the translator and the insulin pump; wherein the translator and the rechargeable battery are disposed within the interior volume.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION

Figure 1:
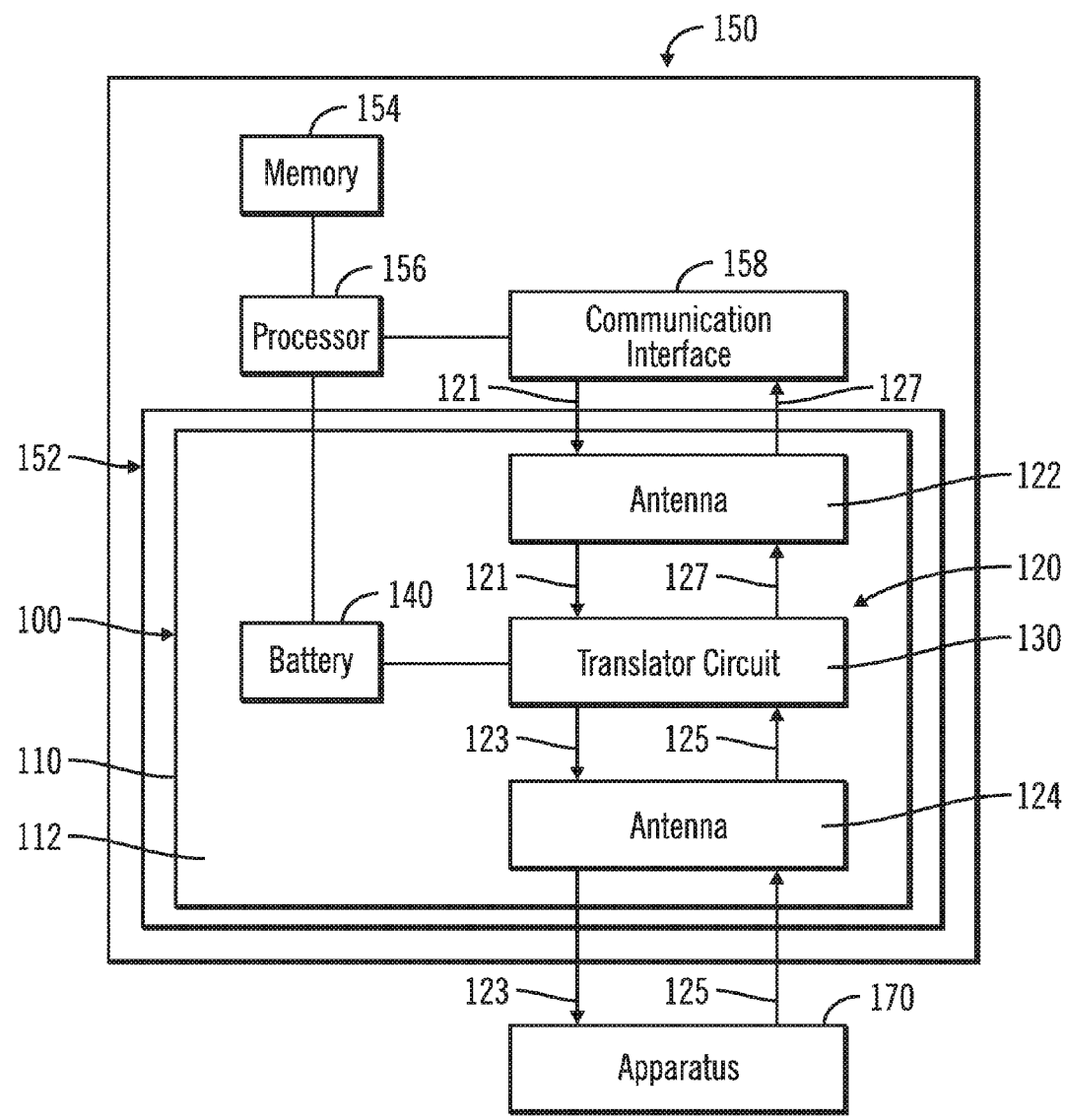
FIG. 1 is a schematic diagram of a protocol translation device made in accordance with the invention.

FIG. 1 is a schematic diagram of a protocol translation device made in accordance with the invention. The protocol translation device fits within the battery compartment of an apparatus and translates a first wireless protocol used by the apparatus to another second wireless protocol, so the apparatus can communicate with another apparatus over the second wireless protocol.

The protocol translation device 100 is for use with a first apparatus 150 having a battery compartment 152 and communicating over a first wireless protocol, and for use with a second apparatus 170 communicating over a second wireless protocol. In this embodiment, the protocol translation device 100 includes a battery casing 110 sized to fit within the battery compartment 152, the battery casing 110 defining an interior volume 112; a translator 120 having a first antenna 122 operable to communicate with the first apparatus 150, a second antenna 124 operable to communicate with the second apparatus 170, and a translator circuit 130 operably connected between the first antenna 122 and the second antenna 124; and a battery 140 operably connected to power the translator. The translator circuit 130 is operable to translate between the first wireless protocol and the second wireless protocol, is operable to communicate with the first antenna 122 on the first wireless protocol, and is operable to communicate with the second antenna 124 on the second wireless protocol. The translator 120 and the battery 140 are disposed within the interior volume 112. In this example, the battery 140 is further operably connected to power the first apparatus 150 in addition to the protocol translation device 100.

In this example, the first apparatus 150 further includes a memory 154 operable to store programming code, a processor 156 operably connected to the memory 154, and a communication interface 158 operably connected to the processor 156. The processor 156 is responsive to the programming code stored in the memory 154 to send and receive wireless signals conforming to the first wireless protocol from the communication interface 158. The processor 156 of the first apparatus 150 can be any processor desired for a particular application. Exemplary processors include a central processing unit and a microprocessor. The processor can include or be attached to auxiliary equipment, such as memory, data storage, additional processors, input/output devices, antennas, and the like, as required to perform various functions.

The communications between the first apparatus 150 and the second apparatus 170 can be described in terms of the signals between the first apparatus 150 and the second apparatus 170. In this embodiment, the communication interface 158 of the first apparatus 150 generates a first-in signal 121 which the first antenna 122 receives and passes to the translator circuit 130. The first-in signal 121 conforms to the first wireless protocol. The translator circuit 130 receives the first-in signal 121 and translates the first-in signal 121 to a second-out signal 123 which the second antenna 124 receives and passes to the second apparatus 170. The second-out signal 123 conforms to the second wireless protocol. In this embodiment, the second apparatus 170 generates a second-in signal 125 which the second antenna 124 receives and passes to the translator circuit 130. The second-in signal 125 conforms to the second wireless protocol. The translator circuit 130 receives the second-in signal 125 and translates the second-in signal 125 to a first-out signal 127 which the first antenna 122 receives and passes to the communication interface 158 of the first apparatus 150. The first-out signal 127 conforms to the first wireless protocol.

The first apparatus 150 and the second apparatus 170 can be any apparatus which the user desires to put in communication. For example, the first apparatus 150 can be an older apparatus designed to communicate on a first wireless protocol incompatible with the second apparatus 170, which is newer and uses a more recently developed second wireless protocol. The protocol translation device 100 translates the first wireless protocol to the second wireless protocol to allow the first apparatus 150 and the second apparatus 170 to communicate.

The first apparatus 150 can be any apparatus communicating over the first wireless protocol and having a battery compartment as desired for a particular application. In one example, the first apparatus 150 is an insulin pump communicating on a 916.5 MHz OOK protocol with a battery compartment sized to fit a AA or AAA battery. In other examples, the first apparatus 150 can be a medical monitoring device, such as a portable heart rate monitor, another drug infusion pump, or the like.

The second apparatus 170 can be any apparatus communicating over the second wireless protocol. In one example, the second apparatus 170 is a smart phone communicating on a Bluetooth protocol and/or 802.11 (WiFi). In other examples, the second apparatus 170 can be a Bluetooth enabled desktop or laptop computer, a tablet device, a smart watch/wearable device, a Bluetooth enabled vehicle information system, a Bluetooth enabled stationary medical monitoring station, or the like.

The first wireless protocol of the first apparatus 150 and the second wireless protocol of the second apparatus 170 can be any wireless protocols for which translation is desired to allow communication between the first apparatus 150 and the second apparatus 170. In one example, the first wireless protocol is a 916.5 MHz OOK protocol and the second wireless protocol is a Bluetooth protocol. In other embodiments, the first wireless protocol can be a protocol following a modulation scheme, such as OOK, 2-FSK, ASK, GFSK, MSK, or the like, on a broadcast band, such as 916.5 MHz, ISM, SRD, MICS (400 MHz), or the like. In other embodiments, the second wireless protocol can be Bluetooth, Bluetooth Low Energy, Zigbee, 802.11 (WiFi), HiperLAN (High Performance Radio LAN), other commercially available protocols and frequencies, or the like.

The protocol translation device 100 includes the battery casing 110; the translator 120 including the first antenna 122, the translator circuit 130, and the second antenna 124.

The battery casing 110 as defined and used herein can be any casing sized to fit within the battery compartment of the first apparatus 150. In one embodiment, the battery casing 110 is same size as a AA battery, a AAA battery, or the like, which is used with the first apparatus 150 during as-designed operation, i.e., for operation with the battery which the first apparatus 150 was originally designed to use. The interior volume 112 of the battery casing 110 receives the translator 120 and the battery 140, and can also receive other components as desired for a particular application. In one embodiment, the protocol translation device 100 is sealed to meet the IPX-8 liquid ingress protection standard.

The first antenna 122 of the translator 120 can be any antenna operable to communicate with the first apparatus 150 on the first wireless protocol. In one embodiment, the first antenna 122 is a 900 MHz antenna. Those skilled in the art will appreciate that additional components can be employed with the first antenna, such as a balun inserted between the first antenna 122 and the translator circuit 130 to balance the transmission line circuit. In one embodiment, the first antenna 122 is incorporated as a trace on the printed circuit board supporting the translator circuit 130.

The second antenna 124 of the translator 120 can be any antenna operable to communicate with the second apparatus 170 on the second wireless protocol. In one embodiment, the second antenna 124 is a Bluetooth antenna. Those skilled in the art will appreciate that additional components can be employed with the second antenna, such as a balun inserted between the second antenna 124 and the translator circuit 130 to balance the transmission line circuit.

The translator circuit 130 can be any circuit operable to translate between the first wireless protocol of the first apparatus 150 and the second wireless protocol of the second apparatus 170. The translator circuit 130 is operable to translate between the first wireless protocol and the second wireless protocol, is operable to communicate with the first antenna 122 on the first wireless protocol, and is operable to communicate with the second antenna 124 on the second wireless protocol. In one embodiment, the main component of the translator circuit 130 is a Programmable Radio-on-Chip with Bluetooth Low Energy (BLE), such as the CYBL10X6X manufactured by Cypress Semiconductor of San Jose, Calif., USA, which incorporates an ARM-core processor. The Programmable Radio-on-Chip with BLE is configurable to communicate with the first apparatus 150 over a number of wireless protocols in the frequency range of 300-900 MHz and to communicate with the second apparatus 170 over a Bluetooth protocol.

The battery 140 is operably connected to power translator circuit 130 of the protocol translation device 100. The battery 140 can be any battery with sufficient voltage and capacity desired for a particular application. Exemplary battery types include nickel-cadmium (NiCd), nickel-zinc (NiZn), nickel metal hydride (NiMH), lithium-ion (Li-ion), lithium polymer, alkaline, and the like. In one embodiment, the battery 140 can be rechargeable. In one embodiment, the battery 140 can operably connected to power the first apparatus 150, such as an insulin pump or the like, so that the protocol translation device 100 replaces the as-designed battery used by the first apparatus 150, i.e., the battery which the first apparatus 150 was originally designed to use. In one embodiment, the battery 140 can have a capacity of 250-300 mAhr. When the battery casing 110 is same size as a AAA battery, the battery 140 can be configured as a stack of button-cell batteries, a half AAA soft cell, or the like.

Figure 2A:
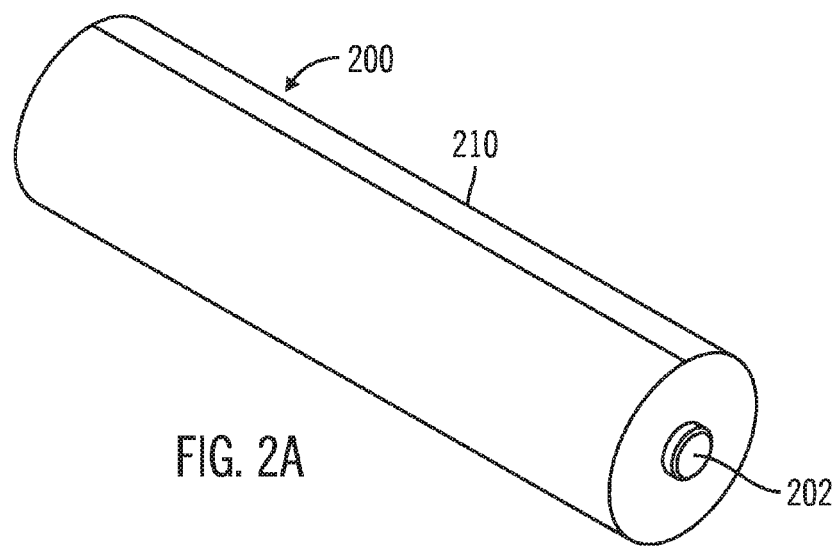
FIGS. 2A & 2B are an external diagram and a cross-section diagram, respectively, of a protocol translation device made in accordance with the invention.
Figure 2B:
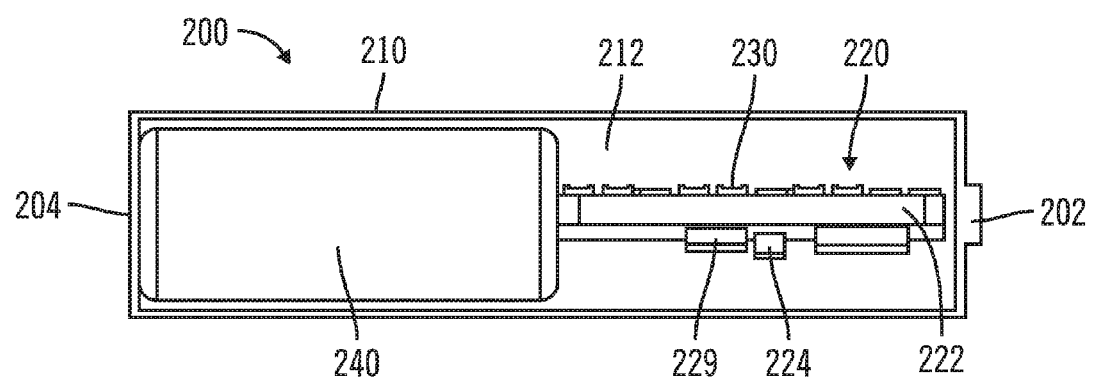

FIGS. 2A & 2B, in which like elements share like reference numbers, are an external diagram and a cross-section diagram, respectively, of a protocol translation device made in accordance with the invention. In this example, the protocol translation device 200 is configured with the battery casing 110 being the same size and configuration as a AAA battery, i.e., having the same form factor. Those skilled in the art will appreciate that the form factor of the battery casing 110 can be the same form factor as that of the original battery designed to be used with the first apparatus.

The protocol translation device 200 includes a battery casing 210 defining an interior volume 212 and having a positive end cap 202 and a negative end cap 204. The translator 220 and the battery 240 are disposed within the interior volume 212. The interior volume 212 can include spacers and/or adapters to receive the protocol translation device components, such as the translator 220 and the battery 240. The translator 220 includes the first antenna 222, the translator circuit 230, and the second antenna 224. In this embodiment, the first antenna 222 is part of the printed circuit board to which the other components of the translator 220 are attached. In this embodiment, the translator circuit 230 also includes a power management chip 229, which governs regulation of the voltage rails VCC powering the components of the translator 220.

The protocol translation device 200 in this example is rechargeable and powers the first apparatus in which it is installed. The power management chip 229 also governs recharging the battery 240 through the positive end cap 202 and a negative end cap 204 to which the terminals of the battery 240 are operably connected. The battery 240 can be recharged by placing the protocol translation device 200 in a standard AAA charger compatible with the chosen chemistry of the battery 240.

Figure 3A:
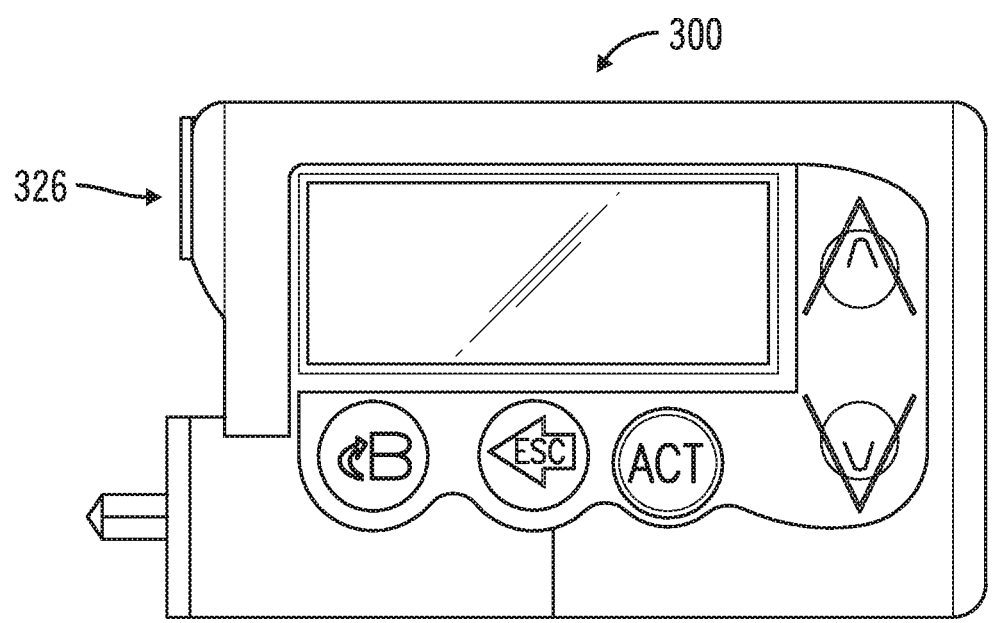
FIGS. 3A & 3B are a depiction and an exploded diagram, respectively, of an insulin pump for use with a protocol translation device made in accordance with the invention.
Figure 3B:
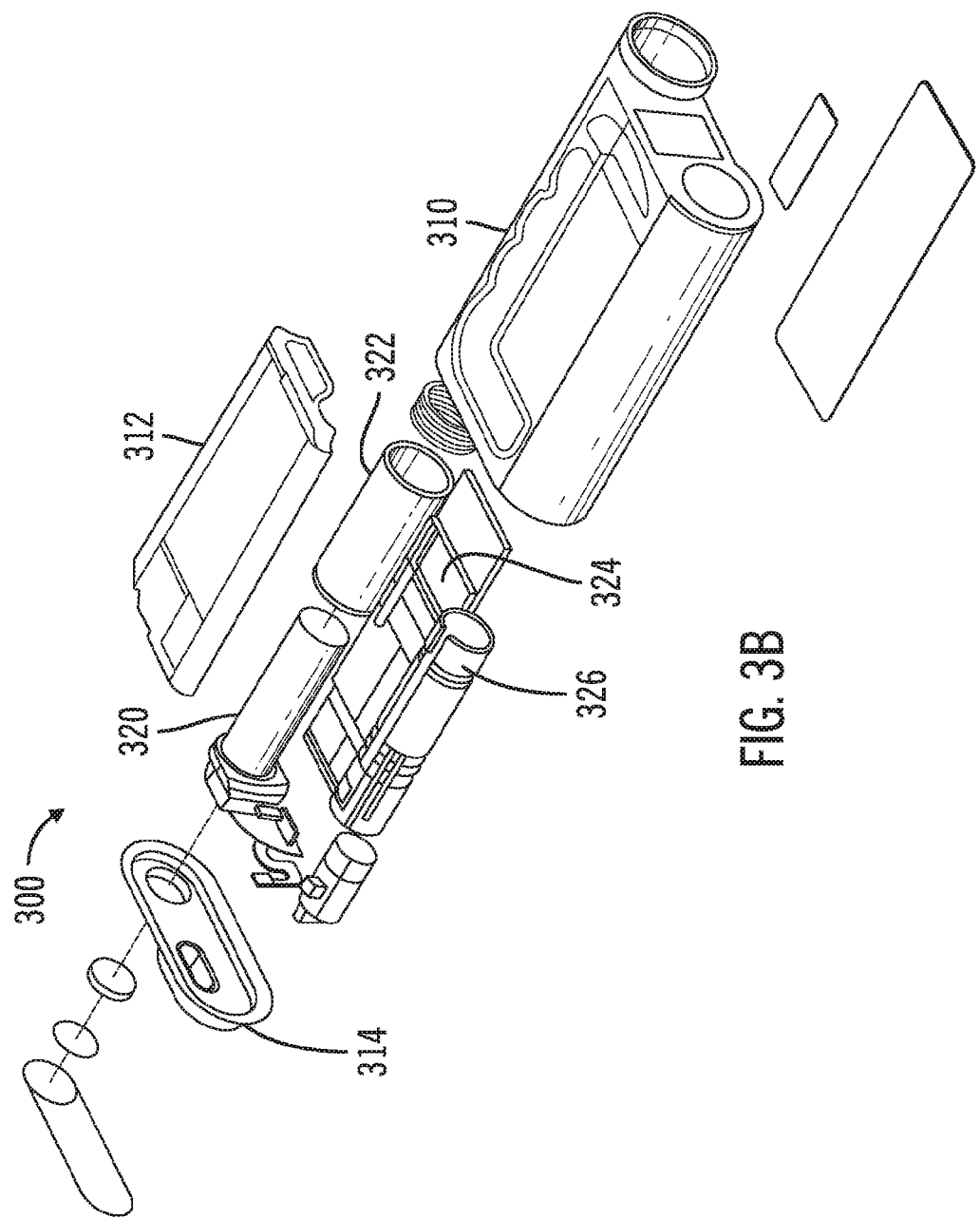

FIGS. 3A & 3B, in which like elements share like reference numbers, are a depiction and an exploded diagram, respectively, of an insulin pump for use with a protocol translation device made in accordance with the invention. The insulin pump is one example of a first apparatus having a battery compartment with which a protocol translation device can be used.

FIG. 3A is a depiction of an insulin pump for use with a protocol translation device made in accordance with the invention. The insulin pump 300 in this example is a Medtronic MiniMed Paradigm Revel™ Insulin Pump. The insulin pump 300 includes a battery compartment 326 for receiving the protocol translation device.

FIG. 3B is an exploded diagram of an insulin pump for use with a protocol translation device made in accordance with the invention. The insulin pump 300 is an example of an apparatus that can be used with the protocol translation device described in conjunction with FIGS. 1, 2A, and 2B above. Those skilled in the art will appreciate that the protocol translation device can be used with any apparatus with a battery compartment.

Referring to FIG. 3B, the insulin pump 300 includes an insulin pump casing 310 with face trim 312 and end cap 314. The insulin pump casing 310 has an insulin pump interior volume operable to receive the insulin pump components, including therapeutic agent receiver 322, insulin pump drive 320, insulin pump electronics 324 operable to control the insulin pump drive 320, and battery compartment 326. A protocol translation device can be placed in the battery compartment 326 of the insulin pump 300.

Figure 4:
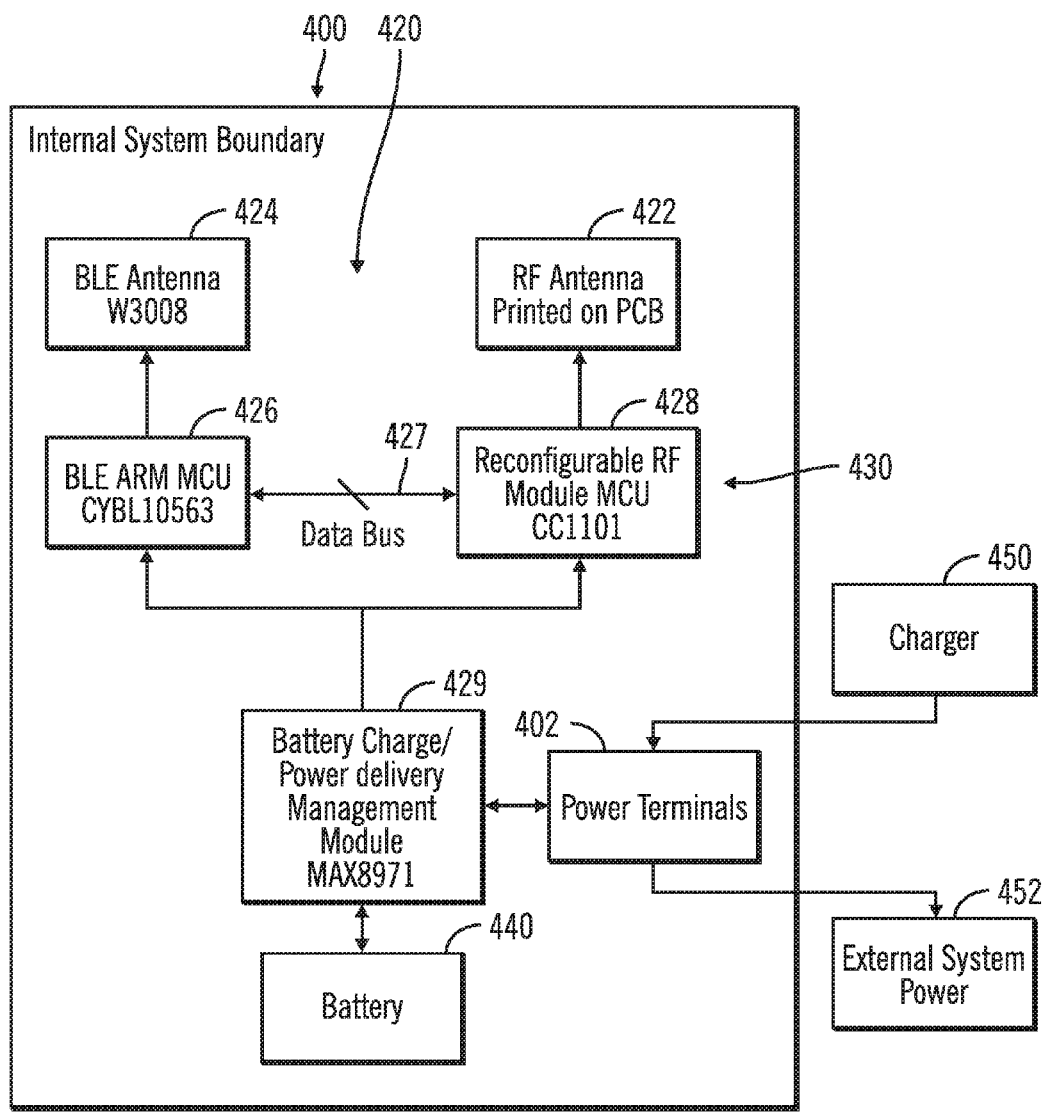
FIG. 4 is another schematic diagram of a protocol translation device made in accordance with the invention.

FIG. 4 is another schematic diagram of a protocol translation device made in accordance with the invention. The protocol translation device 400 includes a translator 420 and a battery 440 disposed within an interior volume of a battery casing. In this embodiment, the translator 420 includes a first antenna (RF antenna) 422, a translator circuit 430, and a second antenna (BLE antenna) 424. The translator circuit 430 includes an RF transceiver (reconfigurable RF module MCU) 428 operably connected to the first antenna 422, a programmable radio-on-chip (BLE ARM MCU) 426 operably connected to the second antenna 424, and a data bus 427 operably connected for communication between the RF transceiver 428 and the programmable radio-on-chip 426. The first antenna 422 can be printed on the printed circuit board to which the other components of the translator 420 are attached.

The translator circuit 430 also includes a power management chip (battery charge/power delivery management module) 429 operably connected to the RF transceiver 428, the programmable radio-on-chip 426, the battery 440, and power terminals 402. The power management chip 429 regulates power to the components of the translator 420 and governs charging of the battery 440 through the power terminals 402 with a removable charger 450, such as a standard AAA charger compatible with the chosen chemistry of the battery 440. Through the power terminals 402, the battery 440 can power an apparatus (external system power) 452 in which the protocol translation device 400 is installed. The removable charger 450 and the apparatus 452 are external to the battery casing of the protocol translation device 400.

Some exemplary components for use in the protocol translation device 400 are as follows: the second antenna 424—W3008 Ceramic 2.4 GHz BT/WLAN/WiFi Antenna manufactured by Pulse Electronics of San Diego, Calif., USA; the programmable radio-on-chip 426—CYBL10563 chip in the CYBL10X6X Programmable Radio-on-Chip With Bluetooth Low Energy (PRoC BLE) family manufactured by Cypress Semiconductor of San Jose, Calif., USA; the RF transceiver 428—CC1101 Low-Power Sub-1 GHz RF Transceiver manufactured by Texas Instruments of Dallas, Tex., USA; and the power management chip 429—MAX8971 1.55A 1-Cell Li+DC-DC Charger manufactured by Maxim Integrated of San Jose, Calif., USA. Those skilled in the art will appreciate that these particular components are for illustration only and that other components can be selected as desired for a particular application.

It is important to note that FIGS. 1-4 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A protocol translation device for use with a first apparatus comprising an insulin pump having a battery compartment and communicating over a first wireless protocol, and for use with a second apparatus communicating over a second wireless protocol, the protocol translation device comprising:
   a battery casing sized to fit within the battery compartment, the battery casing defining an interior volume;
   a translator comprising:
      a first antenna operable to communicate with the first apparatus;
      a second antenna operable to communicate with the second apparatus; and
      a translator circuit operably connected between the first antenna and the second antenna, the translator circuit being operable to translate between the first wireless protocol and the second wireless protocol, being operable to communicate with the first antenna on the first wireless protocol, and being operable to communicate with the second antenna on the second wireless protocol; and
   a battery operably connected to power the first apparatus in addition to the translator of the protocol translation device;
   wherein the translator, which comprises the translator circuit operably connected between the first antenna and the second antenna, and the battery, are all disposed within the interior volume.

2. The protocol translation device of claim 1 wherein the battery is operably connected to power the first apparatus, wherein the battery comprises a stack of button-cell batteries or half AAA soft cells.

3. The protocol translation device of claim 1 wherein the battery is rechargeable.

4. The protocol translation device of claim 1 wherein the battery casing is the same size as a battery selected from the group consisting of a AA battery and a AAA battery.

5. The protocol translation device of claim 1 wherein the first wireless protocol is a 916.5 MHz OOK protocol and the second wireless protocol is a Bluetooth protocol.

6. The protocol translation device of claim 1 wherein the first wireless protocol has a modulation scheme selected from the group consisting of OOK, 2-FSK, ASK, GFSK, and MSK operating on a broadcast band selected from the group consisting of 916.5 MHz, ISM, SRD, and MICS.

7. The protocol translation device of claim 1 wherein the second wireless protocol is selected from the group consisting of Bluetooth, Bluetooth Low Energy, Zigbee, 802.11, and HiperLAN.

8. A protocol translation device for use with a first apparatus comprising an insulin pump having a battery compartment and communicating over a first wireless protocol, and for use with a second apparatus communicating over a second wireless protocol, the protocol translation device comprising:
   a battery casing sized to fit within the battery compartment, the battery casing defining an interior volume;
   a translator comprising:
      a first antenna operable to receive a first-in signal from the first apparatus, the first-in signal conforming to the first wireless protocol;
      a translator circuit operable to receive the first-in signal from the first antenna and operable to translate the first-in signal to a second-out signal conforming to the second wireless protocol; and
      a second antenna operable to receive the second-out signal from the translator circuit and operable to transmit the second-out signal to the second apparatus; and
   a battery operably connected to power the first apparatus in addition to the translator of the protocol translation device;
   wherein the translator, which comprises the translator circuit operably connected between the first antenna and the second antenna, and the battery, are all disposed within the interior volume.

9. The protocol translation device of claim 8 wherein:
   the second antenna is further operable to receive a second-in signal from the second apparatus, the second-in signal conforming to the second wireless protocol;
   the translator circuit is further operable to receive the second-in signal from the second antenna and operable to translate the second-in signal to a first-out signal conforming to the first wireless protocol; and
   the first antenna is further operable to receive the first-out signal from the translator circuit and operable to transmit the first-out signal to the first apparatus.

10. The protocol translation device of claim 8 wherein the battery is operably connected to power the first apparatus, and wherein the battery comprises a stack of button-cell batteries or half AAA soft cells.

11. The protocol translation device of claim 8 wherein the battery is rechargeable.

12. The protocol translation device of claim 8 wherein the battery casing is the same size as a battery selected from the group consisting of a AA battery and a AAA battery.

13. The protocol translation device of claim 8 wherein the first wireless protocol is a 916.5 MHz OOK protocol and the second wireless protocol is a Bluetooth protocol.

14. The protocol translation device of claim 8 wherein the first wireless protocol has a modulation scheme selected from the group consisting of OOK, 2-FSK, ASK, GFSK, and MSK operating on a broadcast band selected from the group consisting of 916.5 MHz, ISM, SRD, and MICS.

15. The protocol translation device of claim 8 wherein the second wireless protocol is selected from the group consisting of Bluetooth, Bluetooth Low Energy, Zigbee, 802.11, and HiperLAN.

16. A protocol translation device for use with an insulin pump having a battery compartment sized to fit a AAA battery and communicating over a 916.5 MHz OOK protocol, and for use with a smart phone communicating over a Bluetooth protocol, the protocol translation device comprising:
- a battery casing sized to a AAA battery form factor, the battery casing defining an interior volume;
- a translator comprising:
  - a first antenna operable to communicate with the insulin pump;
  - a second antenna operable to communicate with the smart phone; and
  - a translator circuit operably connected between the first antenna and the second antenna, the translator circuit being operable to translate between the 916.5 MHz OOK protocol and the Bluetooth protocol, being operable to communicate with the first antenna on the 916.5 MHz OOK protocol, and being operable to communicate with the second antenna on the Bluetooth protocol; and
- a rechargeable battery operably connected to power the translator of the protocol translation device and the insulin pump;
- wherein the translator, which comprises the translator circuit operably connected between the first antenna and the second antenna, and the rechargeable battery, are all disposed within the interior volume.

* * * * *